(12) United States Patent
Henry et al.

(10) Patent No.: US 11,497,844 B2
(45) Date of Patent: Nov. 15, 2022

(54) TRANSANAL IRRIGATION DEVICE AND SYSTEM

(71) Applicant: Hollister Incorporated, Libertyville, IL (US)

(72) Inventors: Jerome A. Henry, Castlebar (IE); William K. Arnold, Gurnee, IL (US); Stephen Collum, Castlebar (IE); Denise Gamblin, Leeds (GB); Ruchi Seth, Libertyville, IL (US); Adam Foley, Swords (IE)

(73) Assignee: Hollister Incorporated, Libertyville, IL (US)

( * ) Notice: Subject to any disclaimer, the term of this patent is extended or adjusted under 35 U.S.C. 154(b) by 317 days.

(21) Appl. No.: 16/467,244

(22) PCT Filed: Dec. 8, 2017

(86) PCT No.: PCT/US2017/065266
§ 371 (c)(1),
(2) Date: Jun. 6, 2019

(87) PCT Pub. No.: WO2018/111713
PCT Pub. Date: Jun. 21, 2018

(65) Prior Publication Data
US 2020/0078510 A1 Mar. 12, 2020

Related U.S. Application Data

(60) Provisional application No. 62/434,143, filed on Dec. 14, 2016.

(51) Int. Cl.
*A61M 3/02* (2006.01)
(52) U.S. Cl.
CPC ........ *A61M 3/0279* (2013.01); *A61M 3/0254* (2013.01); *A61M 3/0262* (2013.01);
(Continued)

(58) Field of Classification Search
CPC .... A61M 3/02; A61M 3/0279; A61M 3/0262; A61M 3/0283; A61M 2210/1064; A61M 2210/1067
See application file for complete search history.

(56) References Cited

U.S. PATENT DOCUMENTS 701,124 A * 5/1902 Allen ................... A61M 3/0283
604/41
1,004,103 A 9/1911 Tacey
(Continued)

FOREIGN PATENT DOCUMENTS

AT 369994 B 2/1983
DE 4114390 A1 11/1992
(Continued)

OTHER PUBLICATIONS

International Search Report and Written Opinion dated May 22, 2018 for International Application No. PCT/US2017/065266.
(Continued)

*Primary Examiner* — Laura A Bouchelle
(74) *Attorney, Agent, or Firm* — Cook Alex Ltd.

(57) ABSTRACT

A device for performing transanal irrigation includes an elongated neck having a proximal end and a flushing liquid channel passing therethrough. In a system including the device, the flushing liquid channel communicates with a source of flushing liquid. An insert is positioned on the proximal end of the neck of the device and is inserted into a body cavity of a user. The insert has a flushing liquid opening that is in fluid communication with the flushing liquid channel of the neck. A control housing is connected to the neck of the device and contains a pump. Pressurized flushing liquid flows through the device channel and exits through the flushing liquid opening of the insert when the pump is activated. A pair of support arms are attached to the
(Continued)

device neck and rest on a sitting user's legs with the insert positioned below a body cavity of the user.

16 Claims, 4 Drawing Sheets

(52) U.S. Cl.
CPC ............... *A61M 2205/3337* (2013.01); *A61M 2205/8206* (2013.01); *A61M 2210/1067* (2013.01)

(56) References Cited

U.S. PATENT DOCUMENTS

| | | | |
|---|---|---|---|
| 1,286,083 A | 11/1918 | Pennington | |
| 1,710,701 A | 4/1929 | Hertzberg | |
| 1,853,202 A | 1/1932 | De Forest | |
| 2,691,373 A | 10/1954 | Bried | |
| 3,653,377 A | 4/1972 | Rebold | |
| 3,731,676 A | 5/1973 | Rebold | |
| 3,794,031 A | 2/1974 | Bloom | |
| 3,802,418 A | 4/1974 | Clayton | |
| 3,854,483 A | 12/1974 | Powers | |
| 3,894,540 A | 7/1975 | Bonner, Jr. | |
| 3,910,274 A | 10/1975 | Nolan | |
| 3,934,722 A | 1/1976 | Goldberg | |
| 4,043,345 A | 8/1977 | Kramann et al. | |
| 4,109,659 A | 8/1978 | Sheridan | |
| 4,117,847 A | 10/1978 | Clayton | |
| 4,682,979 A | 7/1987 | Girouard | |
| 4,890,340 A | 1/1990 | Lovitt | |
| 4,956,298 A | 9/1990 | Diekmann | |
| 5,097,540 A | 3/1992 | Lovitt | |
| 5,149,326 A | 9/1992 | Woodgrift et al. | |
| 5,176,630 A | 1/1993 | Shilling | |
| 5,190,519 A | 3/1993 | Mead | |
| 5,217,114 A | 6/1993 | Gadberry et al. | |
| 5,217,439 A | 6/1993 | McClusky | |
| 5,225,165 A | 7/1993 | Perlman | |
| 5,250,024 A | 10/1993 | Kensey | |
| 5,405,319 A | 4/1995 | Abell | |
| 5,413,561 A | 5/1995 | Fischell et al. | |
| 5,417,326 A | 5/1995 | Winer | |
| 5,443,445 A | 8/1995 | Peters | |
| 5,864,895 A | 2/1999 | Ota | |
| 5,868,265 A | 2/1999 | Kobayashi | |
| 5,881,774 A | 3/1999 | Utterberg | |
| 6,106,506 A | 8/2000 | Abell | |
| 6,125,843 A | 10/2000 | Gold | |
| 6,258,078 B1 | 7/2001 | Thilly | |
| 6,468,245 B2 | 10/2002 | Alexandersen | |
| 6,585,721 B2 | 7/2003 | Fiore | |
| 6,665,888 B1* | 12/2003 | Kwak ................. | A61M 3/0208 4/420.1 |
| 6,751,813 B2 | 6/2004 | Chung | |
| 6,761,702 B2 | 7/2004 | Smith | |
| 6,822,253 B1 | 11/2004 | Martin et al. | |
| 6,908,013 B2 | 6/2005 | Thomson et al. | |
| 6,984,226 B1 | 1/2006 | Abell | |
| 7,120,487 B2 | 10/2006 | Nelson | |
| 7,147,627 B2 | 12/2006 | Kim | |
| 7,438,704 B1 | 10/2008 | Kawashima et al. | |
| 7,546,931 B2 | 6/2009 | Giusti | |
| 7,571,804 B2 | 8/2009 | Kjellmann Bruun et al. | |
| 7,614,514 B2 | 11/2009 | Fuchs | |
| 7,625,355 B2 | 12/2009 | Yu | |
| 7,682,353 B2 | 3/2010 | Tanjhoj | |
| 7,717,284 B2 | 5/2010 | Giusti | |
| 7,748,550 B2 | 7/2010 | Cho | |
| 7,867,220 B2 | 1/2011 | Tanghoj | |
| 7,886,907 B2 | 2/2011 | Murray et al. | |
| 7,914,505 B2 | 3/2011 | Moeller-Jensen | |
| 7,967,744 B2 | 6/2011 | Kaye et al. | |
| 8,137,309 B2 | 3/2012 | Nishtala et al. | |
| 8,172,101 B2 | 5/2012 | Giusti | |
| 8,181,778 B1 | 5/2012 | Van Groningen et al. | |
| 8,230,993 B2 | 7/2012 | Tanghoej | |
| 8,231,589 B2 | 7/2012 | Moeller-Jensen | |
| 8,282,624 B2 | 10/2012 | Tanghoej et al. | |
| 8,361,057 B2 | 1/2013 | Tanghoej et al. | |
| 8,398,615 B2 | 3/2013 | Torstensen et al. | |
| 8,434,639 B2 | 5/2013 | Markert | |
| 8,439,213 B2 | 5/2013 | Goha et al. | |
| 8,448,798 B2 | 5/2013 | Groubert | |
| 8,491,568 B2 | 7/2013 | Schertiger et al. | |
| 8,518,012 B2 | 8/2013 | Smith | |
| 8,568,348 B2 | 10/2013 | Vlodaver | |
| 8,574,206 B2 | 11/2013 | Bjerregaard | |
| 8,579,115 B2 | 11/2013 | Murphy et al. | |
| 8,579,850 B2 | 11/2013 | Bjerregaard | |
| 8,641,687 B2* | 2/2014 | Iparraguirre .......... | A61M 31/00 604/279 |
| 8,657,801 B2 | 2/2014 | Nielsen | |
| 8,752,722 B2 | 6/2014 | Kuhn et al. | |
| 8,863,968 B2 | 10/2014 | Giusti | |
| 8,905,981 B2 | 12/2014 | Budig | |
| 9,352,318 B2 | 5/2016 | Giusti | |
| 9,422,089 B2 | 8/2016 | Wheeler | |
| 2002/0019613 A1 | 2/2002 | Alexandersen | |
| 2003/0073963 A1 | 4/2003 | Falconer | |
| 2003/0073974 A1 | 4/2003 | Falconer | |
| 2004/0260152 A1 | 12/2004 | Sant | |
| 2004/0267198 A1 | 12/2004 | Torstensen | |
| 2005/0070933 A1 | 3/2005 | Leiboff | |
| 2005/0148954 A1 | 7/2005 | Abell | |
| 2005/0277811 A1 | 12/2005 | Richards | |
| 2006/0009732 A1 | 1/2006 | Hardy | |
| 2006/0025728 A1 | 2/2006 | Leiboff | |
| 2006/0025729 A1 | 2/2006 | Leiboff | |
| 2006/0142737 A1 | 6/2006 | Tanghoj | |
| 2006/0180585 A1 | 8/2006 | Cunningham et al. | |
| 2007/0073216 A1 | 3/2007 | McAuliffe | |
| 2008/0033371 A1 | 2/2008 | Updegraff et al. | |
| 2008/0065001 A1 | 3/2008 | DiNucci | |
| 2008/0097384 A1 | 4/2008 | Pacey | |
| 2008/0289984 A1 | 11/2008 | Raven | |
| 2009/0054876 A1 | 2/2009 | Borodulin | |
| 2009/0166361 A1 | 7/2009 | Lourenco | |
| 2010/0106236 A1 | 4/2010 | Nelson | |
| 2010/0211050 A1 | 8/2010 | Luther | |
| 2010/0249752 A1 | 9/2010 | TanghoeJ | |
| 2010/0324540 A1 | 12/2010 | Paulen et al. | |
| 2011/0060317 A1 | 3/2011 | Frojd | |
| 2011/0144588 A1 | 6/2011 | Taylor | |
| 2011/0224653 A1 | 9/2011 | Torstensen | |
| 2011/0282311 A1 | 11/2011 | Nishtala | |
| 2011/0295236 A1 | 12/2011 | Gregory | |
| 2011/0302709 A1 | 12/2011 | Taylor | |
| 2012/0016318 A1 | 1/2012 | Hoang et al. | |
| 2012/0165758 A1 | 6/2012 | Sodo | |
| 2012/0179144 A1 | 7/2012 | Carleo | |
| 2012/0271281 A1 | 10/2012 | Schertiger | |
| 2013/0068767 A1 | 3/2013 | Fraser et al. | |
| 2013/0134123 A1 | 5/2013 | Fraser et al. | |
| 2013/0161344 A1 | 6/2013 | Park et al. | |
| 2013/0218136 A1 | 8/2013 | Tanghoej et al. | |
| 2013/0237920 A1 | 9/2013 | Kokenis | |
| 2013/0245380 A1 | 9/2013 | Vogel | |
| 2013/0289537 A1 | 10/2013 | Schertiger | |
| 2013/0292286 A1 | 11/2013 | Van Groningen | |
| 2013/0331781 A1 | 12/2013 | Andreen | |
| 2014/0005602 A1 | 1/2014 | Andreen | |
| 2014/0155864 A1 | 6/2014 | Andreen | |
| 2014/0262860 A1 | 9/2014 | Hagel | |
| 2014/0263436 A1 | 9/2014 | Gelov et al. | |
| 2014/0276631 A1 | 9/2014 | Gilman | |
| 2014/0360896 A1 | 12/2014 | Torstensen | |
| 2016/0016703 A1 | 1/2016 | Muhlemann | |
| 2016/0023818 A1 | 1/2016 | Gelov et al. | |
| 2016/0059999 A1 | 3/2016 | Fraser et al. | |
| 2016/0114148 A1 | 4/2016 | Holm et al. | |

(56) References Cited

U.S. PATENT DOCUMENTS

2016/0228872 A1 8/2016 Giusti
2017/0127888 A1* 5/2017 Culton, Sr. ............. A47K 7/08

FOREIGN PATENT DOCUMENTS

| | | |
|---|---|---|
| DE | 20117438 U1 | 3/2002 |
| DE | 10213411 A1 | 10/2003 |
| DE | 20317135 U1 | 2/2004 |
| DE | 202005008071 U1 | 7/2005 |
| DE | 202005009946 U1 | 9/2005 |
| DE | 202006013663 U1 | 11/2006 |
| DE | 202010006267 U1 | 11/2010 |
| DE | 202010007433 U1 | 7/2011 |
| DE | 202011107025 | 3/2013 |
| DE | 202011107059 | 3/2013 |
| DE | 102013014483 A1 | 6/2014 |
| EP | 0041487 A | 12/1981 |
| EP | 0134630 A | 3/1985 |
| EP | 0861639 A2 | 9/1998 |
| EP | 0809520 B1 | 4/1999 |
| EP | 0996542 A1 | 5/2000 |
| EP | 1051984 A2 | 11/2000 |
| EP | 1180373 A2 | 2/2002 |
| EP | 1011754 B1 | 9/2004 |
| EP | 1466645 A2 | 10/2004 |
| EP | 1392575 B1 | 9/2005 |
| EP | 1593710 A1 | 11/2005 |
| EP | 1634554 A2 | 3/2006 |
| EP | 1638856 A1 | 3/2006 |
| EP | 1246655 B1 | 5/2006 |
| EP | 1434611 B1 | 6/2006 |
| EP | 1671663 A1 | 6/2006 |
| EP | 1303243 B1 | 1/2007 |
| EP | 1752175 A1 | 2/2007 |
| EP | 1752176 A1 | 2/2007 |
| EP | 1752177 A1 | 2/2007 |
| EP | 1039858 B1 | 5/2007 |
| EP | 1491223 B1 | 5/2007 |
| EP | 1878461 A1 | 1/2008 |
| EP | 1897579 A1 | 3/2008 |
| EP | 1897580 A1 | 3/2008 |
| EP | 1946785 A1 | 7/2008 |
| EP | 1946786 A1 | 7/2008 |
| EP | 1372755 B1 | 8/2008 |
| EP | 0915715 B1 | 9/2008 |
| EP | 1531885 B1 | 10/2008 |
| EP | 1977778 A1 | 10/2008 |
| EP | 1982741 A2 | 10/2008 |
| EP | 1514572 B1 | 12/2008 |
| EP | 2027832 A2 | 2/2009 |
| EP | 2042211 A1 | 4/2009 |
| EP | 2044963 A1 | 4/2009 |
| EP | 2060296 A1 | 5/2009 |
| EP | 2072075 A1 | 6/2009 |
| EP | 2106821 A1 | 10/2009 |
| EP | 2035292 B1 | 5/2010 |
| EP | 2251454 A2 | 11/2010 |
| EP | 2211937 B1 | 7/2011 |
| EP | 2125070 B1 | 4/2012 |
| EP | 2452706 A2 | 5/2012 |
| EP | 2468319 A1 | 6/2012 |
| EP | 2468326 A1 | 6/2012 |
| EP | 2005981 B1 | 9/2012 |
| EP | 1909864 B1 | 10/2012 |
| EP | 2504054 A1 | 10/2012 |
| EP | 2515985 A1 | 10/2012 |
| EP | 2158926 B1 | 5/2013 |
| EP | 2596831 A2 | 5/2013 |
| EP | 2242696 B1 | 6/2013 |
| EP | 2617316 A2 | 7/2013 |
| EP | 2638927 A2 | 9/2013 |
| EP | 2671601 A1 | 12/2013 |
| EP | 2671602 A1 | 12/2013 |
| EP | 2679259 A1 | 1/2014 |
| EP | 2679260 A1 | 1/2014 |
| EP | 2679261 A1 | 1/2014 |
| EP | 2682069 A1 | 1/2014 |
| EP | 2686054 A1 | 1/2014 |
| EP | 2703019 A1 | 3/2014 |
| EP | 2416819 B1 | 8/2014 |
| EP | 1752174 B1 | 9/2014 |
| EP | 2774648 A1 | 9/2014 |
| EP | 2470237 B1 | 10/2014 |
| EP | 3061476 A1 | 8/2016 |
| EP | 2576374 B1 | 9/2016 |
| FR | 2717676 A1 | 9/1995 |
| GB | 2031735 A | 4/1980 |
| GB | 2033231 A | 5/1980 |
| GB | 2322079 A | 8/1998 |
| GB | 2496900 A | 5/2013 |
| JP | 2001025473 | 1/2001 |
| KR | 20110101674 | 7/2012 |
| WO | WO 1987/001596 | 3/1987 |
| WO | WO 96-08219 A1 | 3/1996 |
| WO | WO 9625188 A1 | 8/1996 |
| WO | WO 9631250 A1 | 10/1996 |
| WO | WO 9715335 A1 | 5/1997 |
| WO | WO 97-26937 A1 | 7/1997 |
| WO | WO 97-41811 A1 | 11/1997 |
| WO | WO 9749441 A1 | 12/1997 |
| WO | WO 98-11932 A1 | 3/1998 |
| WO | WO 98-19729 A1 | 5/1998 |
| WO | WO 9820722 A2 | 5/1998 |
| WO | WO 9823312 A1 | 6/1998 |
| WO | WO 99-30761 A1 | 6/1999 |
| WO | WO 9930652 A1 | 6/1999 |
| WO | WO 99-42155 A2 | 8/1999 |
| WO | WO 9959656 A1 | 11/1999 |
| WO | WO 00-16843 A1 | 3/2000 |
| WO | WO 00-30575 A1 | 6/2000 |
| WO | WO 00-47494 A1 | 8/2000 |
| WO | WO 01-43807 A1 | 6/2001 |
| WO | WO 0149345 A1 | 7/2001 |
| WO | WO 01-60255 A1 | 8/2001 |
| WO | WO 02007668 A1 | 1/2002 |
| WO | WO 2002/013887 A1 | 2/2002 |
| WO | WO 02-060361 A2 | 8/2002 |
| WO | WO 02074363 A2 | 9/2002 |
| WO | WO 02-080843 A2 | 10/2002 |
| WO | WO 03-001994 A1 | 1/2003 |
| WO | WO 03-008028 A2 | 1/2003 |
| WO | WO 03-008029 A2 | 1/2003 |
| WO | WO 03-022561 A1 | 3/2003 |
| WO | WO 03030967 A1 | 4/2003 |
| WO | WO 03030968 A1 | 4/2003 |
| WO | WO 03030969 A1 | 4/2003 |
| WO | WO 03-045487 A2 | 6/2003 |
| WO | WO 03-061732 A2 | 7/2003 |
| WO | WO 03063668 A1 | 8/2003 |
| WO | WO 03-092779 A1 | 11/2003 |
| WO | WO 03-097237 A2 | 11/2003 |
| WO | WO 2004/006993 A1 | 1/2004 |
| WO | WO 2004/021890 A1 | 3/2004 |
| WO | WO 2004/032750 A1 | 4/2004 |
| WO | WO 2004/035123 A1 | 4/2004 |
| WO | WO 2004/050155 A1 | 6/2004 |
| WO | WO 2004/054446 A1 | 7/2004 |
| WO | WO 2004/060259 A2 | 7/2004 |
| WO | WO 2004/103153 A2 | 12/2004 |
| WO | WO 2004/112712 A2 | 12/2004 |
| WO | WO 2005/003725 A2 | 1/2005 |
| WO | WO 2005/004964 A1 | 1/2005 |
| WO | WO 2005/004970 A1 | 1/2005 |
| WO | WO 2005/014055 A2 | 2/2005 |
| WO | WO 2005/032617 A2 | 4/2005 |
| WO | WO 2006/005349 A2 | 1/2006 |
| WO | WO 2006/010556 A1 | 2/2006 |
| WO | WO 2006/015223 A2 | 2/2006 |
| WO | WO 2006/017439 A2 | 2/2006 |
| WO | WO 2006/024205 A1 | 3/2006 |
| WO | WO 2006/044249 A2 | 4/2006 |
| WO | WO 2006/044621 A2 | 4/2006 |
| WO | WO 2006/045809 A1 | 5/2006 |
| WO | WO 2006/121183 A1 | 11/2006 |

(56) References Cited

FOREIGN PATENT DOCUMENTS

| | | |
|---|---|---|
| WO | WO 2006/135934 A2 | 12/2006 |
| WO | WO 2007/005851 A2 | 1/2007 |
| WO | WO 2007/022223 A2 | 2/2007 |
| WO | WO 2007/038988 A1 | 4/2007 |
| WO | WO 2007/050685 A2 | 5/2007 |
| WO | WO 2007/081264 A1 | 7/2007 |
| WO | WO 2007/082540 A1 | 7/2007 |
| WO | WO 2007/103995 A2 | 9/2007 |
| WO | WO 2007/106356 A2 | 9/2007 |
| WO | WO 2007/106431 A2 | 9/2007 |
| WO | WO 2007/111891 A2 | 10/2007 |
| WO | WO 2007/121137 A2 | 10/2007 |
| WO | WO 2008/024136 A1 | 2/2008 |
| WO | WO 2008/030999 | 3/2008 |
| WO | WO 2008/039910 A2 | 4/2008 |
| WO | WO 2008/048856 A2 | 4/2008 |
| WO | WO 2008/058160 A2 | 5/2008 |
| WO | WO 2008/087220 A1 | 7/2008 |
| WO | WO 2008/087221 A2 | 7/2008 |
| WO | WO 2008/089081 A1 | 7/2008 |
| WO | WO 2008/090551 A2 | 7/2008 |
| WO | WO 2008/137353 A1 | 11/2008 |
| WO | WO 2009/010975 A1 | 1/2009 |
| WO | WO 2009/015152 A1 | 1/2009 |
| WO | WO 2009/017541 A1 | 2/2009 |
| WO | WO 2009/056906 A1 | 5/2009 |
| WO | WO 2009/066163 A1 | 5/2009 |
| WO | WO 2009/128109 A1 | 10/2009 |
| WO | WO 2009/139878 A1 | 11/2009 |
| WO | WO 2009/144028 A1 | 12/2009 |
| WO | WO 2009/153973 A1 | 12/2009 |
| WO | WO 2010/006620 A1 | 1/2010 |
| WO | WO 2010/047501 A2 | 4/2010 |
| WO | WO 2010/057208 A1 | 5/2010 |
| WO | WO 2010/077980 A1 | 7/2010 |
| WO | WO 2010/115430 A1 | 10/2010 |
| WO | WO 2010/115431 A2 | 10/2010 |
| WO | WO 2010/126586 A1 | 11/2010 |
| WO | WO 2010/130261 A1 | 11/2010 |
| WO | WO 2011/011023 | 1/2011 |
| WO | WO 2011/012323 A1 | 2/2011 |
| WO | WO 2011/019359 A1 | 2/2011 |
| WO | WO 2011/026929 A1 | 3/2011 |
| WO | WO 2011/034911 A1 | 3/2011 |
| WO | WO 2011/075581 A1 | 6/2011 |
| WO | WO 2011/079129 A1 | 6/2011 |
| WO | WO 2011/023196 A1 | 8/2011 |
| WO | WO 2011/105644 A1 | 9/2011 |
| WO | WO 2011/109393 A1 | 9/2011 |
| WO | WO 2011/139498 A1 | 11/2011 |
| WO | WO 2011/147803 A1 | 12/2011 |
| WO | WO 2012/006629 A2 | 1/2012 |
| WO | WO 2012/013662 A1 | 2/2012 |
| WO | WO 2012/016179 A1 | 2/2012 |
| WO | WO 2012/016570 A2 | 2/2012 |
| WO | WO 2012/016571 A2 | 2/2012 |
| WO | WO 2012/079590 A1 | 6/2012 |
| WO | WO 2012/085107 A2 | 6/2012 |
| WO | WO 2012/110755 A2 | 8/2012 |
| WO | WO 12120456 A2 | 9/2012 |
| WO | WO 2012/134804 A1 | 10/2012 |
| WO | WO 2012/154946 A1 | 11/2012 |
| WO | WO 2012/156478 A1 | 11/2012 |
| WO | WO 2012/164559 A1 | 12/2012 |
| WO | WO 2012/166045 A1 | 12/2012 |
| WO | WO 2012/166967 A1 | 12/2012 |
| WO | WO 2013/026564 A1 | 2/2013 |
| WO | WO 2013/026565 A1 | 2/2013 |
| WO | WO 2013/029620 A1 | 3/2013 |
| WO | WO 2013/029621 A1 | 3/2013 |
| WO | WO 2013/029622 A1 | 3/2013 |
| WO | WO 2013/075725 A1 | 5/2013 |
| WO | WO 2013/076446 A1 | 5/2013 |
| WO | WO 2013/083137 A1 | 6/2013 |
| WO | WO 2013/090778 A1 | 6/2013 |
| WO | WO 2013/098190 A1 | 7/2013 |
| WO | WO 2013/105091 A1 | 7/2013 |
| WO | WO 2013/163364 A1 | 10/2013 |
| WO | WO 2013/182593 A1 | 12/2013 |
| WO | WO 2013/184158 A1 | 12/2013 |
| WO | WO 2014/001292 A1 | 1/2014 |
| WO | WO 2014/001313 A1 | 1/2014 |
| WO | WO 2014/001322 A1 | 1/2014 |
| WO | WO 2014/062225 A1 | 4/2014 |
| WO | WO 2014/063711 A1 | 5/2014 |
| WO | WO 2014/064414 A1 | 5/2014 |
| WO | WO 2014/074142 A1 | 5/2014 |
| WO | WO 2014/074147 A1 | 5/2014 |
| WO | WO 2014/081859 A1 | 5/2014 |
| WO | WO 2014/085597 A1 | 6/2014 |
| WO | WO 2014/089278 A1 | 6/2014 |
| WO | WO 2014/093056 A1 | 6/2014 |
| WO | WO 2014/139767 | 9/2014 |
| WO | WO 2014/140328 A1 | 9/2014 |
| WO | WO 2014/142895 A1 | 9/2014 |
| WO | WO 2014/142917 A1 | 9/2014 |
| WO | WO 2014/142923 A1 | 9/2014 |
| WO | WO 2014/142930 A1 | 9/2014 |
| WO | WO 2014/144714 | 9/2014 |
| WO | WO 2014/145211 A2 | 9/2014 |
| WO | WO 2014/147620 A1 | 9/2014 |
| WO | WO 2014/149276 A1 | 9/2014 |
| WO | WO 2014/159869 A2 | 10/2014 |
| WO | WO 2014/165046 A1 | 10/2014 |
| WO | WO 2014/176486 A1 | 10/2014 |
| WO | WO 2014/076867 A1 | 11/2014 |
| WO | 2015031851 A2 | 3/2015 |
| WO | WO 15031851 A2 | 3/2015 |
| WO | WO 2015/117141 A1 | 8/2015 |
| WO | WO 2015/184365 | 12/2015 |

OTHER PUBLICATIONS

European Extended Search Report dated Dec. 11, 2020 for European Application No. 20192635.9.

* cited by examiner

TRANSANAL IRRIGATION DEVICE AND SYSTEM

CROSS-REFERENCE TO RELATED APPLICATIONS

The present application is the U.S. National Stage Application of PCT Application No. PCT/US2017/065266, filed Dec. 8, 2017, which claims the benefit of and priority to U.S. Provisional Patent Application No. 62/434,143, filed Dec. 14, 2016, the contents of which are hereby incorporated by reference.

FIELD OF THE INVENTION

The present disclosure relates generally to body cavity irrigation devices, methods and systems and, in particular, to a transanal irrigation device that includes an extended handle that is usable by patients possessing a wide range of dexterity levels and systems that use such a device.

BACKGROUND

Transanal irrigation (TAI) is a process used by individuals who have bowel management issues, such as incontinence, constipation or other neurogenic bowel dysfunction (NBD). Alternatively, TAI may be used for regular bowel evacuations by individuals who are incapacitated due to illness or other medical conditions or injuries (such as spinal cord injury) and thus lack the mobility to access a toilet. During TAI, water or other lavage liquid is introduced into the rectum and colon through a device positioned through the anus so that feces are flushed and evacuated. This creates pseudo-continence for the patient/user. Furthermore, individuals that are bedridden may develop fecal impaction. Such bowel obstructions may be removed via TAI.

Systems for performing TAI currently on the market allow the user to introduce water into the bowel through a rectal catheter while the user sits on a toilet or a commode/shower chair or lays in a bed. The user introduces an amount of water or other liquid into the bowel (typically 500-700 mL) in order to flush out stool located in the bowel passage. The user typically introduces the water, waits for a period of time and then allows gravity to flush the water and stool out of the body.

For TAI users, independence, dexterity, and ease of use are important needs that must be addressed by a TAI system or method.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a device for performing transanal irrigation includes an elongated neck having a proximal end and a flushing liquid channel passing therethrough. The flushing liquid channel is adapted to communicate with a source of flushing liquid. An insert is positioned on the proximal end of the neck and is adapted to be inserted into a body cavity of a user. The insert has a flushing liquid opening that is in fluid communication with the flushing liquid channel of the neck. A control housing is connected to the neck. A pump is positioned within the control housing and is configured so that when the pump is activated, pressurized flushing liquid is able to flow through the flushing liquid channel and exit through the flushing liquid opening of the insert. A pair of support arms are attached to the neck and configured to rest on a sitting user's legs with the insert positioned below a body cavity of the user.

In another aspect, a system for performing transanal irrigation includes a liquid pressurizing device configured to contain and pressurize a supply of flushing liquid. The system also includes a transanal irrigation device having an elongated neck having a proximal end and a flushing liquid channel passing therethrough. The flushing liquid channel is in fluid communication with the liquid pressurizing device. An insert is positioned on the proximal end of the neck and is adapted to be inserted into a body cavity of a user. The insert also has a flushing liquid opening that is in fluid communication with the flushing liquid channel of the neck. A control housing is connected to the neck. A pump is positioned within the control housing and configured so that when the pump is activated, pressurized flushing liquid from the liquid pressurizing device flows through the flushing liquid channel and exits through the flushing liquid opening of the insert.

In yet another aspect, a device for performing transanal irrigation includes an elongated neck having a proximal end and a flushing liquid channel passing therethrough. The flushing liquid channel is adapted to communicate with a source of flushing liquid. An insert is positioned on the proximal end of the neck and has a core having a sidewall and a tip. The tip includes a flushing liquid opening that is in fluid communication with the flushing liquid channel of the neck. The insert also includes a flexible body surrounding an exterior surface of the sidewall in a spaced fashion so that an annular chamber is defined. The annular chamber is adapted to contain a lubricant and the flexible body includes a pore. A control housing is connected to the neck of the device. A pump is positioned within the control housing and is configured so that when the pump is activated, pressurized flushing liquid is able to flow through the flushing liquid channel and exit through the flushing liquid opening of the insert.

DETAILED DESCRIPTION OF EMBODIMENTS

Figure 1:
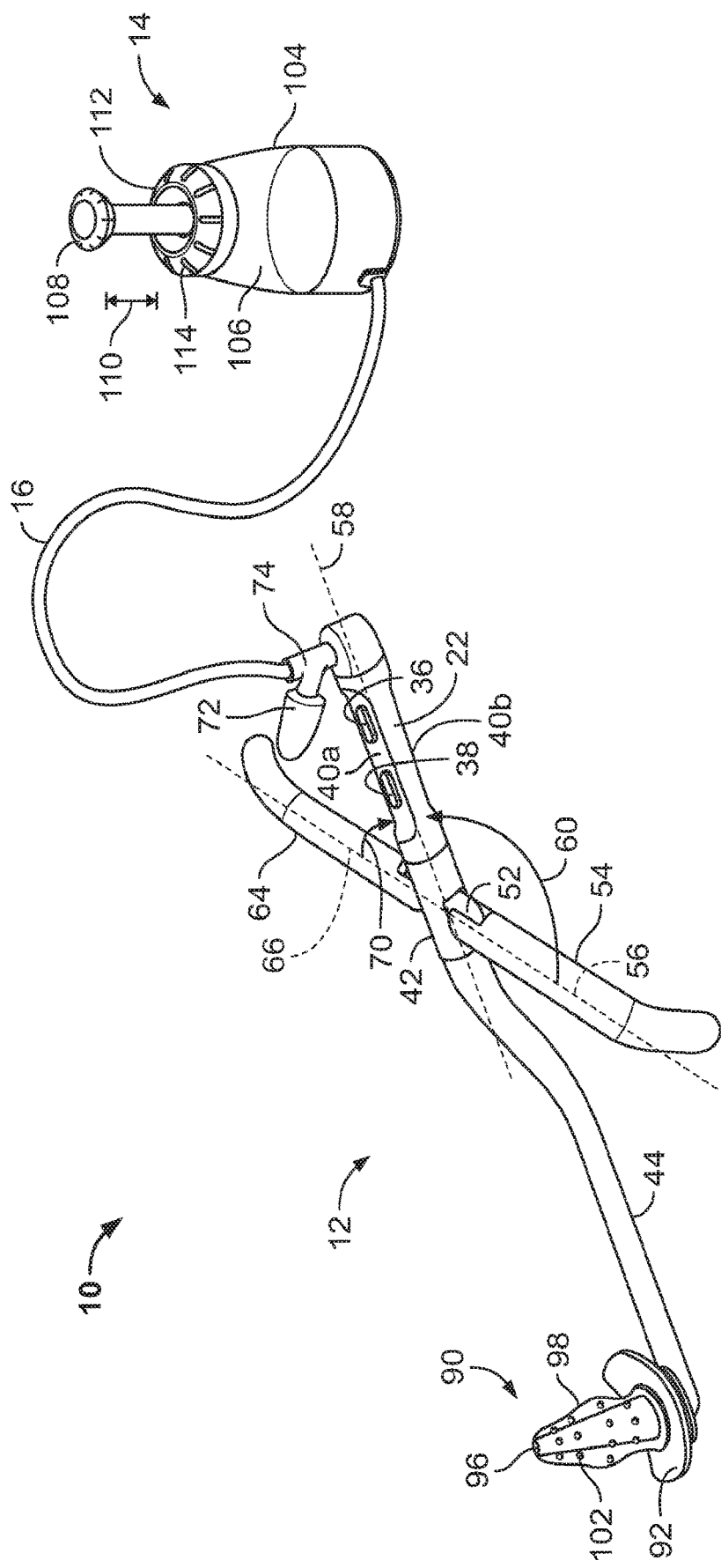
FIG. 1 is a perspective view of an embodiment of a transanal irrigation system.

An embodiment of a transanal irrigation (TAI) system is indicated in general at 10 in FIG. 1. The system includes a transanal irrigation device, indicated in general at 12, a liquid pressurizing device, indicated in general at 14, and a tubing or tube line 16 connecting the two components 12 and 14.

While the invention is described below in terms of use as a transanal irrigation device and system, it is to be understood that the invention could be used to irrigate other body cavities of a user including, but not limited to, stomas and body cavities accessible by stomas.

Figure 2:
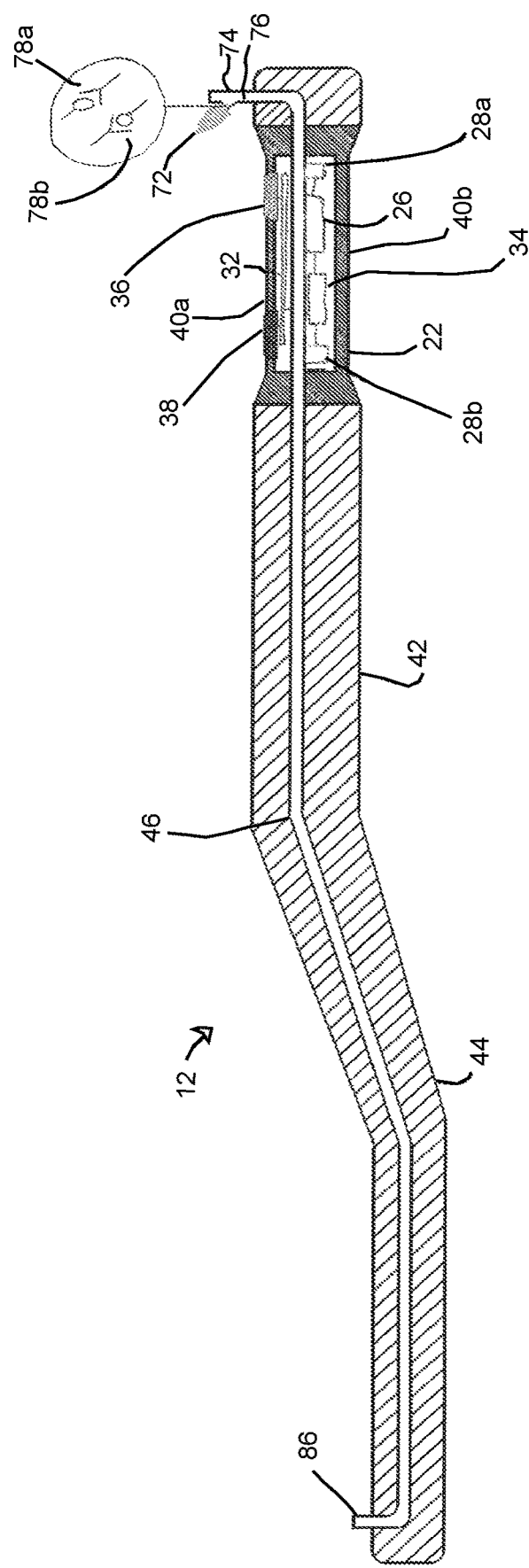
FIG. 2 is an enlarged cross sectional view of the transanal irrigation device of FIG. 1.

As illustrated in FIGS. 1 and 2, the TAI device 12 takes the form of a wand and includes a control housing 22. As illustrated in FIG. 2, the control housing includes a chamber that houses a pump 26, inlet and outlet valves 28a and 28b, control circuitry 32 and a battery 34. Inlet and outlet valves 28a and 28b may be solenoid operated valves or alternative types of automatic valves. Alternatively, manual valves may be used. A power on/off button or switch 36 and an activate/deactivate pump button or switch 38 are mounted in the control housing 22 as well. The top and bottom surfaces of the control housing 22 include recesses 40a and 40b so that the control housing may function as a handle.

An intermediate portion 42 is attached to the proximal end of the control housing 22, while an elongated neck portion 44 is attached to the proximal end of the intermediate portion 42. As illustrated in FIG. 2, a flushing liquid channel 46 extends through each of the control housing 22, intermediate portion 42 and neck portion 44. The control housing 22, intermediate portion 42 and neck portion 44 may be integrally molded as a single piece, such as from plastic, or they may be formed as separate components that are joined together. In addition, the flushing liquid channel may be integrally molded within the control housing, intermediate portion and neck portion, or it may be separately formed as a tube that is positioned within these components.

As illustrated in FIG. 1, the intermediate portion 42 includes an ear or tab 52 to which is pivotally mounted a support arm 54. The pivot connection permits the support arm 54 to be folded between a use position, shown in FIG. 1, where the longitudinal axis 56 of the support arm 54 is generally perpendicular to the longitudinal axis 58 of the intermediate portion 42 and the control housing 22, and a transport or storage position, where the arm 54 is positioned adjacent to the intermediate portion 42 and the control housing 22 with longitudinal axes 56 and 58 parallel to one another. This folding action is illustrated by arrow 60 of FIG. 1.

Support arm 64 is pivotally mounted to the intermediate portion 42 in a similar fashion and features a longitudinal axis 66. As indicated by arrow 70 of FIG. 1, the support arm 64 also folds between the use position shown in FIG. 1 to a transport or storage position where the longitudinal axis 66 is parallel to longitudinal axis 58.

A squeeze bulb 72 is mounted on a fitting 74. As illustrated in FIG. 1, tubing line 16 is connected to the fitting 74. As shown in FIG. 2, fitting 74 includes a passage 76 that is in fluid communication with flushing liquid channel 46. A pair of check valves, illustrated at 78a and 78b in FIG. 2, are positioned between the interior chamber of the squeeze bulb 72 and the passage 76 of the fitting 74.

Figure 3:
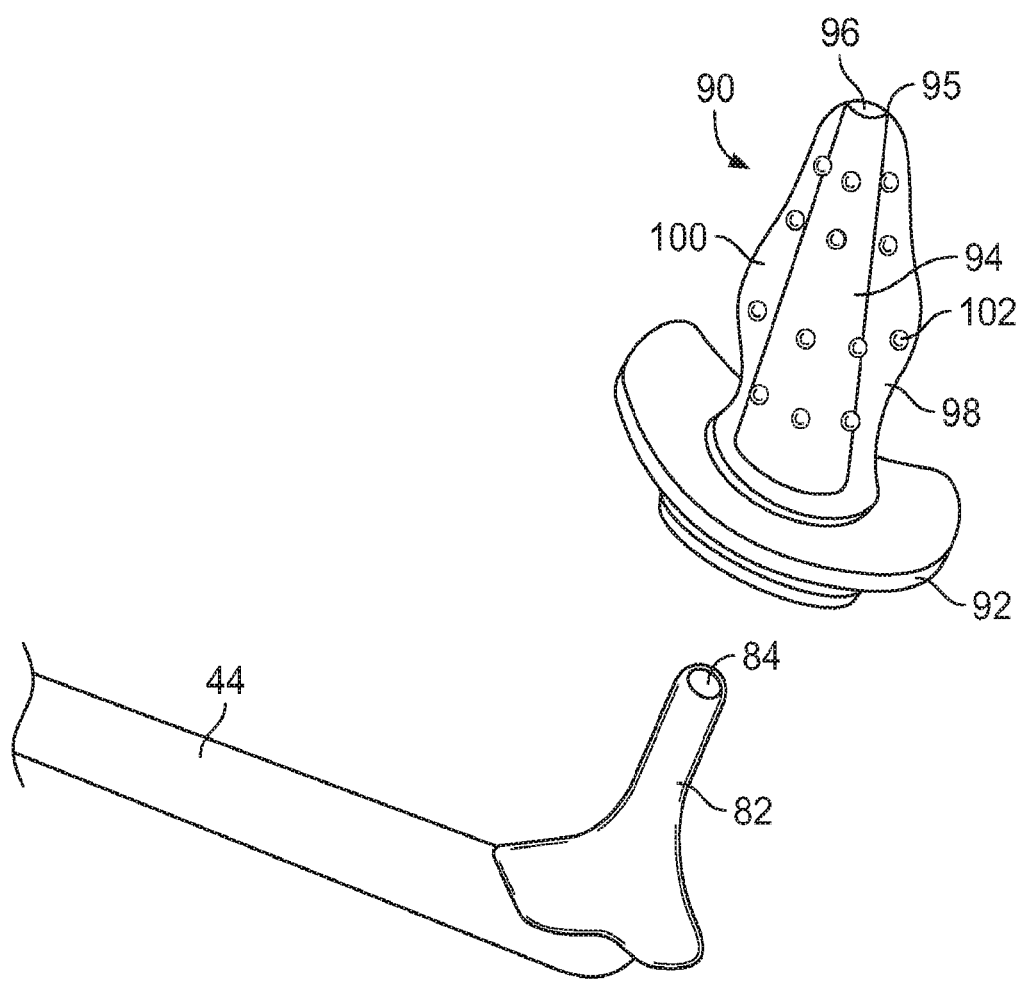
FIG. 3 is an enlarged perspective exploded view of the proximal end of the transanal irrigation device and the insert of FIG. 1.
Figure 4:
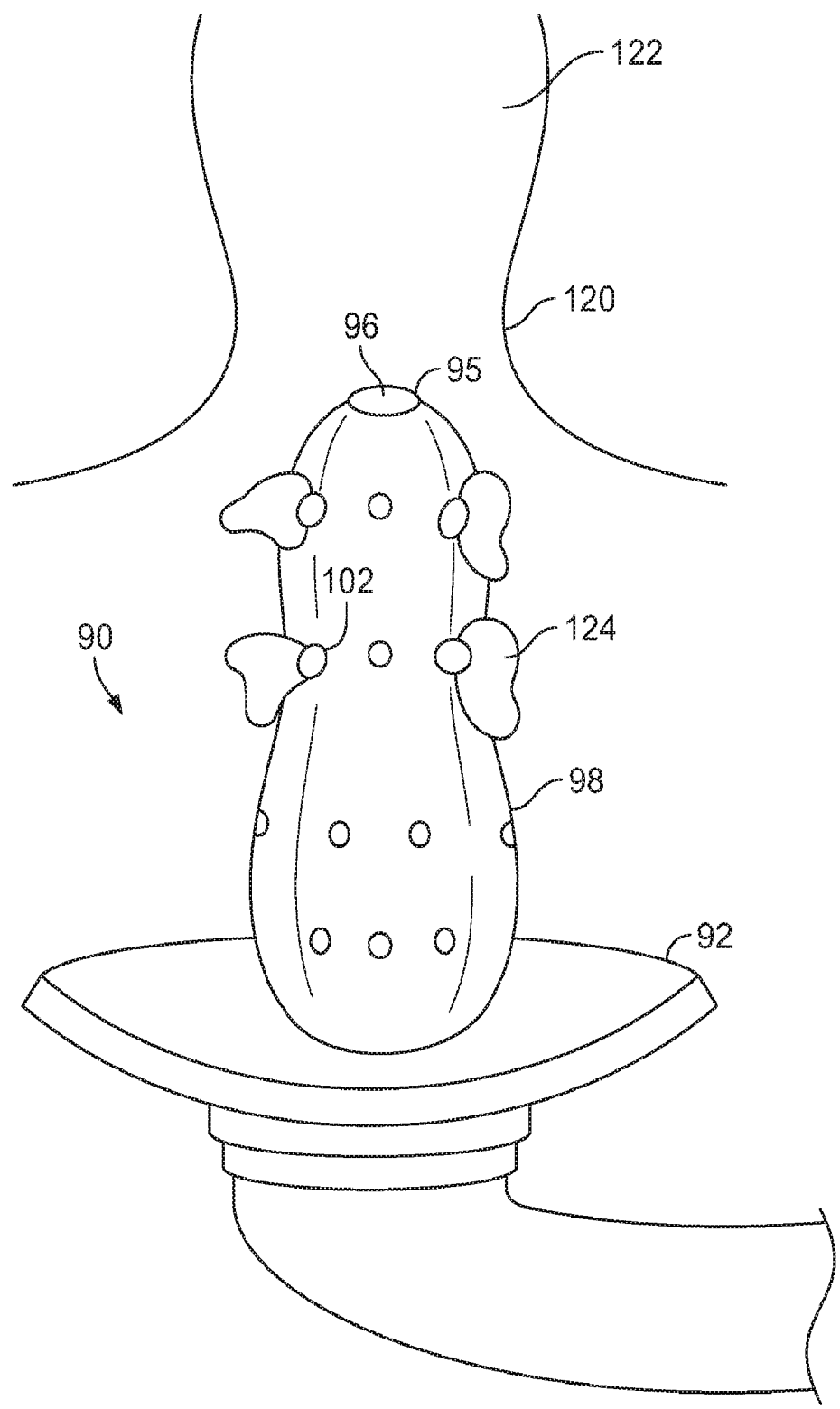
FIG. 4 is a perspective view of the insert of FIGS. 1 and 3.

With reference to FIG. 3, the proximal end of the neck portion 44 is provided with an insert mount 82 that features a passage 84. Passage 84 is in fluid communication with the flushing liquid channel 46 (FIG. 2) via fitting 86. As illustrated in FIGS. 1, 3 and 4, a disposable insert cone, indicated in general at 90, is removably positioned on the insert mount 82. The insert cone 90 includes a combination shield and stop 92 and a generally cone-shaped (or frusto-conical) core 94. Core 94 may feature alternative shapes such as cylindrical. Core 94 includes a tip 95 that is provided with a flushing liquid opening 96. Flushing liquid opening 96 is in fluid communication with the passage 84 of the insert mount 82 when the insert cone 90 is positioned thereon.

As shown in FIGS. 1, 3 and 4, a flexible body 98 surrounds the exterior surface of the sidewall of the core 94 and is circumferentially attached to the tip 95 so as to surround, but not obstruct, flushing liquid opening 96. The bottom of the flexible body is joined to the combination shield and stop 92 so as to be circumferentially spaced from the base of the core 94 and define an annular chamber 100 (FIG. 3). The annular chamber 100 is filled with a lubricating gel. The flexible body 98, which may be made of a material such as silicone, rubber or the like, is provided with a number of pores 102.

Alternative heads may be positioned on the insert mount 82 in an interchangeable fashion. For example, a flushable pre-check head, which may or may not be cone-shaped, may be used.

As noted previously, with reference to FIG. 1, a liquid pressurizing device 14 is joined to the TAI device 12 via tube line 16. The liquid pressurizing device 14 features a body 104 which houses a flushing liquid reservoir 106. The reservoir 106 contains a supply of flushing liquid, such as water. A handle 108 may be actuated by the user, as indicated by arrows 110, to activate a pressurizing feature of the device 14. As a result, the flushing liquid inside of the reservoir 106 is pressurized and flows to the TAI device 12. Additional details regarding the liquid pressurizing device 14 may be found in International Patent Application No. PCT/US2014/053573 (International Publ. No. WO 2015/031851) to Hollister Incorporated, filed Aug. 29, 2014, the contents of which are hereby incorporated by reference. Alternative types of pressurizing devices and/or reservoirs known in the art may be used instead.

In operation, the flushing liquid within the liquid pressurizing device 14 is pressurized. The insert cone 90 is positioned on the proximal end of the device 12, as illustrated in FIG. 1, and the support arms 54 and 64 are placed in the use positions illustrated in FIG. 1. The user then sits on a toilet, grasps the handle (control housing 22) and passes the neck portion 44 of the device between his or her legs so that the insert cone 90 is positioned below the anus 120, as shown in FIG. 4. The user then rests the support arms 54 and 64 (FIG. 1) on the tops of his or her thighs so that a fulcrum is formed, and the TAI device 12 may be moved by the user as a lever or in a see-saw fashion.

The user next moves the handle (control housing 22) downwards so that the proximal end of the neck portion 44, and thus the insert cone 90, rises towards the anus 120 (FIG. 4). As the user continues to move the handle 22 downwards, the insert cone 90 passes through the anus 120 and into the rectum 122 (FIG. 4). As this occurs, the flexible body 98 of the insert cone is compressed by the anus and rectum and gel (124 in FIG. 4) is eluted through pores 102 of the insert. As a result, the surface of the insert cone 90 is lubricated thus easing insertion.

Once the insert cone 90 is inserted into the anus and rectum, the user may initiate flow of the flushing liquid through the flushing liquid channel 46 (FIG. 2) of the TAI device 12 by first turning on the device by pressing power on/off button 36. This opens the solenoid operated inlet and outlet valves 28a and 28b. Next, the user presses pump activation/deactivation button 38, which activates the pump 26 (FIG. 2). As a result, pressurized flushing liquid flows from the liquid pressurizing device 14, through tube line 16, through the flushing liquid channel 46 of the TAI device 12, out of opening 96 of the insert cone 90 and into the patient's rectum. After a period of time, the user again presses the pump activation/deactivation button 38 to deactivate the pump and stop the flow of flushing liquid into the rectum.

The user then presses the power on/off button to close the inlet and outlet valves 28*a* and 28*b*.

After a period of time, the user pulls up on the handle 22 so that the insert cone 90 is removed from the user's rectum and anus, and the flushing liquid and fecal matter drain by gravity into the toilet.

If the user finds that the pump 26 is too powerful and/or is more comfortable using a manual pumping mechanism, the squeeze bulb 72 (FIGS. 1 and 2) may be used to deliver the flushing liquid to the user's rectum instead. More specifically, the user presses the power on/off button 36 to open the solenoid operated valves 28*a* and 28*b*, but does not press the pump activation/deactivation button 38.

The user then repetitively squeezes and releases the squeeze bulb 72. Due to the check valves 78*a* and 78*b* (FIG. 2), flushing liquid from the liquid pressurizing device 14 (and tube line 16) is drawn into the interior chamber of the squeeze bulb 72 and then expelled in an alternating fashion so that the liquid is pumped through the flushing liquid channel 46 of the TAI device 12, out of the opening 96 of the insert cone 90 and into the patient's rectum. The user then presses the power on/off button to close the inlet and outlet valves 28*a* and 28*b*.

The user may also wish to use the squeeze bulb 72 to add additional flushing liquid to the rectum after the pump 26 is used.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. A device for performing transanal irrigation comprising:
    a. an elongated neck having a proximal end and a flushing liquid channel passing therethrough, said flushing liquid channel adapted to communicate with a source of flushing liquid;
    b. an insert positioned on the proximal end of the neck, said insert adapted to be inserted into a body cavity of a user and having a flushing liquid opening that is in fluid communication with the flushing liquid channel of the neck;
    c. a handle connected to the neck;
    d. a pair of support arms attached to the neck and configured to rest on a sitting user's legs with the insert positioned below a body cavity of the user; and
    e. an intermediate portion positioned between and attached to the neck and the handle, and wherein the pair of support arms are pivotally attached to the intermediate portion.

2. The device of claim 1 wherein the pair of support arms are pivotally attached to the neck so as to pivot between a use position and a transport position.

3. The device of claim 1 wherein the flushing liquid channel passes through the neck, intermediate portion and the handle.

4. The device of claim 1 further comprising a pump configured so that when the pump is activated, pressurized flushing liquid is able to flow through the flushing liquid channel and exit through the flushing liquid opening of the insert.

5. The device of claim 4 further comprising an inlet valve that permits liquid to flow through the flushing liquid channel when open.

6. A device for performing transanal irrigation comprising:
    a. an elongated neck having a proximal end and a flushing liquid channel passing therethrough, said flushing liquid channel adapted to communicate with a source of flushing liquid;
    b. an insert positioned on the proximal end of the neck, said insert adapted to be inserted into a body cavity of a user and having a flushing liquid opening that is in fluid communication with the flushing liquid channel of the neck;
    c. a handle connected to the neck;
    d. a pair of support arms attached to the neck and configured to rest on a sitting user's legs with the insert positioned below a body cavity of the user; and
    e. a pump configured so that when the pump is activated, pressurized flushing liquid is able to flow through the flushing liquid channel and exit through the flushing liquid opening of the insert; and
    wherein the handle includes a control housing and the pump is positioned within the control housing.

7. The device of claim 6 wherein the control housing also contains an inlet valve that permits liquid to flow through the flushing liquid channel when open.

8. The device of claim 7 wherein the valve is solenoid operated.

9. The device of claim 6 wherein the control housing further contains a battery, control circuitry and a switch to operate the pump.

10. The device of claim 1 further comprising a squeeze bulb in fluid communication with the flushing liquid channel.

11. The device of claim 10 wherein the squeeze bulb is in fluid communication with the flushing liquid channel via a pair of check valves configured so that flushing liquid may be drawn into and expelled from the squeeze bulb in an alternating fashion.

12. The device of claim 1 wherein the insert is removably attached to the proximal end of the neck.

13. The device of claim 1 wherein the insert includes:
    i) a core having a sidewall and a tip, said tip including a flushing liquid opening that is in fluid communication with the flushing liquid channel of the neck; and
    ii) a flexible body surrounding an exterior surface of the sidewall in a spaced fashion so that an annular chamber is defined, said annular chamber adapted to contain a lubricant and said flexible body including a pore.

14. A system for performing transanal irrigation comprising:
    a. a liquid pressurizing device configured to contain and pressurize a supply of flushing liquid;
    b. a transanal irrigation device including:
        i) an elongated neck having a proximal end and a flushing liquid channel passing therethrough, said flushing liquid channel in fluid communication with the liquid pressurizing device;
        ii) an insert positioned on the proximal end of the neck, said insert adapted to be inserted into a body cavity of a user and having a flushing liquid opening that is in fluid communication with the flushing liquid channel of the neck;
        iii) a handle connected to the neck and including a control housing;
        iv) a pump positioned within the control housing and configured so that when the pump is activated, pressurized flushing liquid from the liquid pressurizing device flows through the flushing liquid channel and exits through the flushing liquid opening of the insert; and v) a pair of support arms attached to the neck and configured to rest on a sitting user's legs with the insert positioned below a body cavity of the user.

15. The system of claim 14 wherein the insert includes:

i) a core having a sidewall and a tip, said tip including a flushing liquid opening that is in fluid communication with the flushing liquid channel of the neck; and ii) a flexible body surrounding an exterior surface of the sidewall in a spaced fashion so that an annular chamber is defined, said annular chamber adapted to contain a lubricant and said flexible body including a pore.

16. The system of claim 14 wherein the insert is removably attached to the proximal end of the neck.

* * * * *